(12) United States Patent
Hsieh et al.

(10) Patent No.: US 11,291,744 B2
(45) Date of Patent: Apr. 5, 2022

(54) ELECTRODE COMPONENT FOR GENERATING LARGE AREA ATMOSPHERIC PRESSURE PLASMA

(71) Applicant: MING CHI UNIVERSITY OF TECHNOLOGY, New Taipei (TW)

(72) Inventors: Jang-Hsing Hsieh, New Taipei (TW); Shu-Chien Chang, New Taipei (TW); Shi-Wei Huang, New Taipei (TW)

(73) Assignee: Ming Chi University of Technology, New Taipei (TW)

( * ) Notice: Subject to any disclaimer, the term of this patent is extended or adjusted under 35 U.S.C. 154(b) by 128 days.

(21) Appl. No.: 16/827,215

(22) Filed: Mar. 23, 2020

(65) Prior Publication Data

US 2021/0068242 A1    Mar. 4, 2021

(30) Foreign Application Priority Data

Aug. 28, 2019    (TW) ................................. 108130848

(51) Int. Cl.
     *A61L 9/22*      (2006.01)
     *H05H 1/46*      (2006.01)
     (Continued)

(52) U.S. Cl.
     CPC ........ *A61L 9/22* (2013.01); *A61L 2/14* (2013.01); *E06B 7/28* (2013.01); *H01J 19/08* (2013.01);
     (Continued)

(58) Field of Classification Search
CPC ........... H05H 1/2406; H05H 2001/466; H05H 2001/2431; H05H 2001/2468; H01J 37/04; H01J 37/32412; A61L 2/14; A61L 2209/11; A61L 9/22; A61L 2202/11; A61L 1227/54; B01J 19/08; B01J 19/088; C01B 13/11; C08J 7/06; C08J 9/36; B32B 9/04; A61B 18/042
See application file for complete search history.

(56) References Cited

U.S. PATENT DOCUMENTS

| | | | | |
|---|---|---|---|---|
| 4,686,110 A | * | 8/1987 | Endo | ...................... H05B 33/22 313/506 |
| 4,779,960 A | * | 10/1988 | Kozaki | .................. C09K 19/42 349/180 |

(Continued)

*Primary Examiner* — Abdullah A Riyami
*Assistant Examiner* — Syed M Kaiser
(74) *Attorney, Agent, or Firm* — Muncy, Geissler, Olds & Lowe, P.C.

(57) ABSTRACT

An electrode component for generating large area atmosphere pressure plasma is provided. The electrode component comprises a first transparent insulation substrate, a first transparent electrode pattern, a second transparent electrode pattern, and a second transparent insulation substrate. The first transparent insulation substrate has a first thickness. The first transparent electrode pattern and the second transparent electrode pattern are formed on the upper surface of the first transparent insulation substrate and has a gap therebetween. The second transparent insulation substrate has a second thickness and covers the first transparent electrode pattern and the second transparent electrode pattern. The first thickness is greater than the second thickness in order to form atmospheric pressure plasma above the second transparent insulation substrate.

7 Claims, 2 Drawing Sheets

(51) Int. Cl.
*E06B 7/28* (2006.01)
*H05H 1/24* (2006.01)
*H01J 19/08* (2006.01)
*A61L 2/14* (2006.01)

(52) U.S. Cl.
CPC ........ *H05H 1/2406* (2013.01); *A61L 2209/11* (2013.01); *H05H 1/2431* (2021.05); *H05H 1/466* (2021.05)

(56) References Cited

U.S. PATENT DOCUMENTS

| | | | | |
|---|---|---|---|---|
| 6,771,239 | B1* | 8/2004 | Uchiyama | G02F 1/13394 345/87 |
| 8,169,589 | B2* | 5/2012 | Tsi-Shi | G02B 3/14 349/200 |
| 2003/0197474 | A1* | 10/2003 | Kang | G09G 3/298 315/169.4 |
| 2003/0222571 | A1* | 12/2003 | Hara | G09G 3/367 313/500 |
| 2004/0137280 | A1* | 7/2004 | Abe | H01L 31/1884 428/702 |
| 2004/0144558 | A1* | 7/2004 | Zhengkai | H05B 33/10 174/102 R |
| 2005/0255327 | A1* | 11/2005 | Chaney | A61L 27/54 428/448 |
| 2010/0145253 | A1* | 6/2010 | Gutsol | A61N 1/40 604/20 |
| 2011/0168259 | A1* | 7/2011 | Murata | H01L 31/076 136/258 |
| 2012/0100524 | A1* | 4/2012 | Fridman | B01J 19/087 435/2 |
| 2012/0259272 | A1* | 10/2012 | Staack | A61L 2/14 604/24 |
| 2012/0291706 | A1* | 11/2012 | Kobayashi | H05H 1/2406 118/723 E |
| 2012/0292610 | A1* | 11/2012 | Wang | H01L 27/1259 257/43 |
| 2013/0147340 | A1* | 6/2013 | Holbeche | H01J 37/32825 313/231.31 |
| 2013/0265510 | A1* | 10/2013 | Fang | G02B 30/24 349/15 |
| 2013/0345620 | A1* | 12/2013 | Zemel | A61B 18/042 604/24 |
| 2015/0116270 | A1* | 4/2015 | Kanna | G06F 3/0445 345/174 |
| 2015/0123091 | A1* | 5/2015 | Hakii | H01L 51/5234 257/40 |
| 2015/0259842 | A1* | 9/2015 | Kulyk | D06M 10/025 26/51 |
| 2015/0340207 | A1* | 11/2015 | Holbeche | H01J 37/32825 156/345.33 |
| 2016/0014905 | A1* | 1/2016 | Tsunekawa | B32B 37/02 345/173 |
| 2016/0111676 | A1* | 4/2016 | Ishidai | H01L 51/524 257/40 |
| 2016/0365392 | A1* | 12/2016 | Li | H01L 27/3232 |
| 2017/0308198 | A1* | 10/2017 | Yoon | G06F 3/0445 |
| 2018/0066361 | A1* | 3/2018 | Nara | C23C 16/448 |
| 2019/0006614 | A1* | 1/2019 | Kuroki | H05B 33/28 |
| 2019/0155424 | A1* | 5/2019 | Nukui | G06F 3/0412 |
| 2019/0377457 | A1* | 12/2019 | Nakayama | G06F 3/0448 |
| 2021/0022234 | A1* | 1/2021 | Polak | A61B 18/042 |

* cited by examiner

ELECTRODE COMPONENT FOR GENERATING LARGE AREA ATMOSPHERIC PRESSURE PLASMA

BACKGROUND OF INVENTION

1. Field of the Invention

The present invention is related to an atmospheric pressure plasma apparatus, and more particularly is related to an electrode component for generating large area atmospheric pressure plasma.

2. Description of the Prior Art

In recent years, atmospheric plasma has been utilized, as a non-intrusive method, for revitalizing and treating human skin.

However, traditional atmospheric pressure plasma apparatus is too large facilitate biomedical applications. The huge apparatus may put the stress to the patient. In addition, it is difficult for the doctor to check the condition of the affected region in real time when doing large area plasma treatment or sterilization.

SUMMARY OF THE INVENTION

Accordingly, it is an object of the present invention to provide an electrode component for generating large area atmospheric pressure plasma, which allows the user to check the plasma treating area directly through the electrode component.

In accordance with an embodiment of the present invention, an electrode component for generating large area atmosphere pressure plasma is provided. The electrode component comprises a first transparent insulation substrate, a first transparent electrode pattern, a second transparent electrode pattern, and a second transparent insulation substrate. The first transparent insulation substrate has a first thickness. The first transparent electrode pattern and the second transparent electrode pattern are formed on an upper surface of the first transparent insulation substrate and has a gap therebetween. The second transparent insulation substrate has a second thickness and covers the first transparent electrode pattern and the second transparent electrode pattern. The first thickness is greater than the second thickness in order to form large area atmospheric pressure plasma above the second transparent insulation substrate.

In compared with the conventional technology, the electrode component 30, 40 in accordance with the present invention may be fabricated by using the mature panel manufacturing process. The structure of the electrode component 30, 40 is simple, and thus is easy for user's handheld operation. In addition, because the electrode component 30, 40 is substantially transparent, the user may check the condition of the affected region (e.g. the wound) through the electrode component 30, 40 directly. Moreover, the transparent design may demonstrate a better visual feeling to the patient to relieve the repellency to atmospheric pressure plasma treatment.

BRIEF DESCRIPTION OF THE DRAWINGS

The present invention will now be specified with reference to its preferred embodiment illustrated in the drawings, in which.

DESCRIPTION OF THE PREFERRED EMBODIMENT

Figure 1:
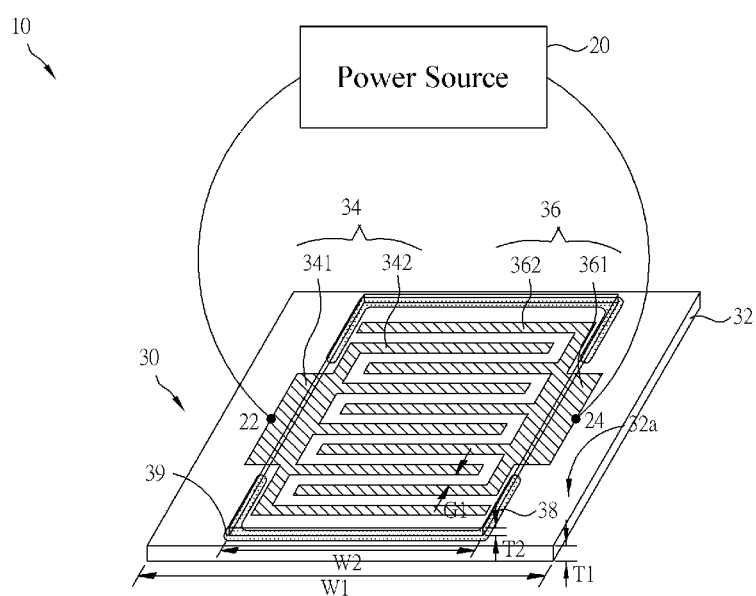
FIG. 1 is a schematic view showing the arrangement of an atmospheric pressure plasma apparatus in accordance with an embodiment of the present invention.

FIG. 1 is a schematic view showing the arrangement of a low temperature atmospheric pressure plasma apparatus in accordance with an embodiment of the present invention. As shown, the atmospheric pressure plasma apparatus 10 comprises a power source 20 and an electrode component 30.

The power source 20 has a high voltage end 22 (e.g. the live wire) and a low voltage end 24 (e.g. the grounded wire) for outputting a high voltage pulse to the electrode component 30 for generating atmospheric pressure plasma. The power source 20 may adjust the voltage level of the pulse supplied to the electrode component 30 to control the strength of the atmospheric pressure plasma to be generated. In an embodiment of the present invention, the power source may be an AC power source. However, the present invention should not be restricted thereto. The other types of power source with the capability of generating high voltage pulses to the electrode component 30 can also be applied in the present invention. Moreover, in an embodiment of the present invention, the electrode component 30 may be placed within the atmosphere. However, the present invention should not be restricted thereto. In the other embodiments of the present invention, the electrode component 30 may generate the atmospheric pressure plasma by using the inert gas as the working gas.

The electrode component 30 comprises a first transparent insulation substrate 32, a first transparent electrode pattern 34, a second transparent electrode pattern 36, and a second transparent insulation substrate 38. The first transparent insulation substrate 32 has a first thickness T1. The first transparent electrode pattern 34 and the second transparent electrode pattern 36 are formed on an upper surface 32a of the first transparent insulation substrate 32. The second transparent insulation substrate 38 has a second thickness T2, and covers the first transparent electrode pattern 34 and the second transparent electrode pattern 36.

The first transparent electrode pattern 34 comprises a power connection portion 341 and a plurality of first stripe-shaped transparent electrodes 342. The second transparent electrode pattern 36 comprises a power connection portion 361 and a plurality of second stripe-shaped transparent electrodes 362. The power connection portion 341 and the power connection portion 361 are connected to the high voltage end 22 and the low voltage end 24 of the power source 20 respectively.

The first stripe-shaped transparent electrodes 342 and the second stripe-shaped transparent electrodes 362 are alternately arranged and placed on the upper surface 32a of the first transparent insulation substrate 32. Each first stripe-shaped transparent electrode 342 is spaced apart from the neighboring second stripe-shaped transparent electrode 362 by gap G1 for generating electric field to induce atmospheric pressure plasma. Based on the arrangement of the alternately placed first stripe-shaped transparent electrodes 342 and the second stripe-shaped transparent electrodes 362, the region with atmospheric pressure plasma can be defined and the uniformity of atmospheric pressure plasma within the region can be enhanced. In the present embodiment, a square atmospheric pressure plasma treating region may be defined by the alternately arranged first stripe-shaped transparent electrodes 342 and the second stripe-shaped transparent electrodes 362.

In an embodiment, the gap G1 between the first transparent electrode pattern 34 and the second transparent electrode pattern 36 may be ranged between 0.8~1.2 mm. In an embodiment, the first transparent electrode pattern 34 and the second transparent electrode pattern 36 may be made of a material selected from the group composed of indium tin oxide (ITO), indium zinc oxide (IZO) and indium gallium zinc oxide (IGZO). In addition, in order to keep high transparency, the thickness of the first transparent electrode pattern 34 and the second transparent electrode pattern 36 should not be too large. In an embodiment of the present invention, the thickness of the first transparent electrode pattern 34 and the second transparent electrode pattern 36 may be about 200 nm.

In the present embodiment, the first transparent insulation substrate 32 is a quartz glass substrate, and the second transparent insulation substrate 38 is also a quartz glass substrate. The two transparent insulation substrates 32 and 38 are made of the same material. However, the thickness of the first transparent insulation substrate 32, i.e. the first thickness T1, is greater than the thickness of the second transparent insulation substrate 38, i.e. the second thickness T2. With the thickness difference between the first transparent insulation substrate 32 and the second transparent insulation substrate 38, large area plasma would be generated at the side outside the second transparent insulation substrate 38 (i.e. the position above the second transparent insulation substrate 38 in the figure), and the atmospheric plasma generated at the side outside the first transparent insulation substrate 32 (i.e. the position below the first transparent insulation substrate 33 in the figure) would be prohibited. In an embodiment, the first thickness T1 of the first transparent insulation substrate 32 may be about 0.7 mm, and the second thickness T2 of the second transparent insulation substrate 38 may be about 0.5 mm.

In the present embodiment, quartz glass is selected for forming the first transparent insulation substrate 32 and the second transparent insulation substrate 38 to provide a better mechanical strength. However, the present invention should not be restricted thereto. In the other embodiments, the first transparent insulation substrate 32 and the second transparent insulation substrate 38 may be made of the other transparent dielectric materials. In an embodiment, the first transparent insulation substrate 32 and the second transparent insulation substrate 38 may be made of different dielectric materials with different dielectric constants so as to decide the generation of atmospheric pressure plasma (the atmospheric pressure plasma would be generated at the side with a lower dielectric constant).

In the present embodiment, the power connection portion 341 of the first transparent electrode pattern 34 and the power connection portion 361 of the second transparent electrode pattern 36 are located at two opposite sides of the first transparent insulation substrate 32. The width W1 of the first transparent insulation substrate 32 is greater than the width W2 of the second transparent substrate 38 such that the power connection portion 341 of the first transparent electrode pattern 34 and the power connection portion 361 of the second transparent electrode pattern 36 may be exposed to facilitate the connection to the high voltage end 22 and the low voltage end 24 of the power source 20. However, the present invention should not be restricted thereto. In an embodiment, the power connection portions 341 and 361 may be located at two neighboring sides of the first transparent insulation substrate 32, or at the same side. In addition, in an embodiment, the size of the second transparent insulation substrate 38 may be adjusted in accordance with the positions of the power connection portions 341 and 361.

In the electrode component 30 of the present embodiment, the width W1 of the first transparent insulation substrate 32 is greater than the width W2 of the second transparent insulation substrate 38 so as to have the power connection portion 341 of the first transparent electrode pattern 34 and the power connection portion 361 of the second transparent electrode pattern 36 exposed to connect the power source 20. However, the present invention should not be restricted thereto. In another embodiment, at least one open may be formed in the second transparent insulation substrate 38 to expose the power connection portion 341 of the first transparent electrode pattern 34 and the power connection portion 361 of the second transparent electrode pattern 36.

In an embodiment of the present invention, in order to have the second transparent insulation substrate 38 fixed on the first transparent insulation substrate 32, the electrode component 30 may have an adhesive layer 39 interposed between the first transparent insulation substrate 32 and the second transparent insulation substrate 38, and placed outside the first transparent electrode pattern 34 and the second transparent electrode pattern 36. As an exemplary embodiment, the adhesive layer 39 may be made of transparent adhesive materials, such as epoxy.

Figure 2:
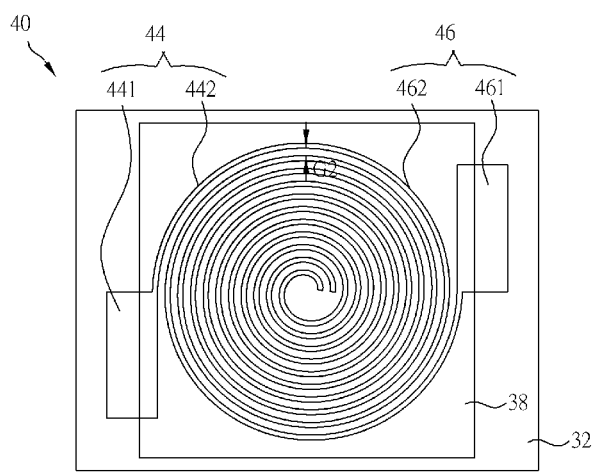
FIG. 2 is a top schematic view showing the electrode component in accordance with another embodiment of the present invention.

FIG. 2 is a top view showing the electrode component in accordance with another embodiment of the present invention. In compared with the electrode component 30 shown in FIG. 1, the electrode component 40 in accordance with the present embodiment comprises a first transparent electrode pattern 44 and a second transparent electrode pattern 46.

The first transparent electrode pattern 44 comprises a power connection portion 441 and a spiral-shaped transparent electrode 442, and the second transparent electrode pattern 46 comprises a power connection portion 461 and a spiral-shaped transparent electrode 462. The power connection portion 441 and the power connection portion 461 are utilized for connecting to the high voltage end 22 and low voltage end 24 of the power source 20 respectively.

The first spiral-shaped transparent electrode 442 and the second spiral-shaped transparent electrode 462 are twisted together but have a gap G2 kept therebetween. A circular atmospheric pressure plasma treating region would be defined by the first spiral-shaped transparent electrode 442 and the second spiral-shaped transparent electrode 462.

In general, with an adequate gap G1, G2 being kept between the first transparent electrode pattern 34, 44 and the second transparent electrode pattern 36, 46 (e.g. 0.8~1.2 mm), the shape and the distribution of the first transparent electrode pattern 34, 44 and the second transparent electrode pattern 36, 46 may be adjusted according to the need in practice. For example, as a rectangular atmospheric pressure plasma treating region is demanded, the embodiment shown in FIG. 1 of the present application may be referred with the adjustment of changing the size parameters of the first stripe-shaped transparent electrodes 342 and the second stripe-shaped transparent electrodes 362 to cover a rectangular region; and the embodiment shown in FIG. 2 of the present application may also be referred to cover a rectangular region by using two rectangular spiral shaped transparent electrodes.

In compared with the conventional technology, the electrode component 30, 40 in accordance with the present invention may be fabricated by using the mature panel manufacturing process. The structure of the electrode component 30, 40 is simple, and thus is easy for user's handheld operation. In addition, because the electrode component 30, 40 is substantially transparent, the user may check the condition of the affected region (e.g. the wound) through the electrode component 30, 40 directly. Moreover, the transparent design may demonstrate a better visual feeling to the patient to relieve the repellency to atmospheric pressure plasma treatment.

While the present invention has been particularly shown and described with reference to a preferred embodiment, it will be understood by those skilled in the art that various changes in form and detail may be without departing from the spirit and scope of the present invention.

What is claimed is:

1. An electrode component for generating large area atmospheric pressure plasma comprising:
    a first transparent insulation substrate with a first thickness;
    a first transparent electrode pattern, formed on an upper surface of the first transparent insulation substrate;
    a second transparent electrode pattern, formed on the upper surface, and the first transparent electrode pattern and the second transparent electrode pattern having a gap therebetween, wherein the first transparent electrode pattern and the second transparent electrode pattern do not overlap;
    a second transparent insulation substrate with a second thickness, covering the first transparent electrode pattern and the second transparent electrode pattern; and
    a transparent adhesive layer, interposed between the first transparent insulation substrate and the second transparent insulation substrate, and placed outside the first transparent electrode pattern and the second transparent electrode pattern;
    wherein the first thickness is greater than the second thickness in order to form the large area atmospheric pressure plasma above the second transparent insulation substrate.

2. The electrode component of claim 1, wherein the first transparent insulation substrate and the second transparent insulation substrate are quartz glass substrates.

3. The electrode component of claim 1, wherein the first transparent electrode pattern and the second transparent electrode pattern are made of a material selected from a group composed of ITO, IZO, and IGZO.

4. The electrode component of claim 1, wherein a thickness of the first transparent electrode pattern or the second transparent electrode pattern is smaller than the second thickness.

5. The electrode component of claim 1, wherein the gap is ranged between 0.8~1.2 mm.

6. The electrode component of claim 1, wherein the first transparent electrode pattern comprises a first spiral-shaped transparent electrode, the second transparent electrode pattern comprises a second spiral-shaped transparent electrode, and the first spiral-shaped transparent electrode and the second spiral-shaped transparent electrode are twisted together.

7. The electrode component of claim 1, wherein the first transparent electrode pattern comprises a plurality of first stripe-shaped transparent electrodes, the second transparent electrode pattern comprises a plurality of second stripe-shaped transparent electrodes, and the first stripe-shaped transparent electrodes and the second stripe-shaped transparent electrodes are alternately arranged on the upper surface.

* * * * *